United States Patent
Bourg, Jr. et al.

(10) Patent No.: US 8,284,248 B2
(45) Date of Patent: Oct. 9, 2012

(54) METHOD FOR REAL TIME DETECTION OF DEFECTS IN A FOOD PRODUCT

(75) Inventors: Wilfred Marcellien Bourg, Jr., Melissa, TX (US); Enrique Michel, Dallas, TX (US)

(73) Assignee: Frito-Lay North America, Inc., Plano, TX (US)

( * ) Notice: Subject to any disclaimer, the term of this patent is extended or adjusted under 35 U.S.C. 154(b) by 459 days.

(21) Appl. No.: 12/547,075

(22) Filed: Aug. 25, 2009

(65) Prior Publication Data

US 2011/0050880 A1 Mar. 3, 2011

(51) Int. Cl.
*H04N 7/18* (2006.01)

(52) U.S. Cl. .............. 348/89; 348/E7.085; 382/110

(58) Field of Classification Search .............. 348/89; 382/110
See application file for complete search history.

(56) References Cited

U.S. PATENT DOCUMENTS

| | | | |
|---|---|---|---|
| 1,053 A | 12/1838 | Hatfield |
| 1,782,960 A | 11/1930 | Erysin |
| 2,448,152 A | 8/1948 | Patton |
| 2,490,431 A | 12/1949 | Greene |
| 2,498,024 A | 2/1950 | Baxter |
| 2,584,893 A | 2/1952 | Lloyd |
| 2,611,705 A | 9/1952 | Hendel |
| 2,704,257 A | 3/1955 | deSellano |
| 2,744,017 A | 5/1956 | Baldwin |
| 2,759,832 A | 8/1956 | Cording, Jr. |
| 2,762,709 A | 9/1956 | Janis |
| 2,780,552 A | 2/1957 | Willard |
| 2,893,878 A | 7/1959 | Simon |
| 2,905,559 A | 9/1959 | Anderson |
| 2,910,367 A | 10/1959 | Melnick |
| 2,987,401 A | 6/1961 | Johnston |
| 3,026,885 A | 3/1962 | Eytinge |
| 3,027,258 A | 3/1962 | Markakis |
| 3,038,810 A | 6/1962 | Akerboom |
| 3,044,880 A | 7/1962 | Bogyo |
| 3,085,020 A | 4/1963 | Backinger |
| 3,219,458 A | 11/1965 | Higby |
| 3,278,311 A | 10/1966 | Brown |

(Continued)

FOREIGN PATENT DOCUMENTS

CL  4032002  6/2003

(Continued)

OTHER PUBLICATIONS

Decision of Rejection, Japanese Pat. App. No. 2007-544461 dated Mar. 16, 2010, translated into English (2 pages).

(Continued)

*Primary Examiner* — Yves Dalencourt
(74) *Attorney, Agent, or Firm* — James R. Gourley; Colin P. Cahoon; Carstens & Cahoon, LLP

(57) ABSTRACT

The present invention is a method to detect defects in a process producing a food product by utilizing multivariate image analysis. In one aspect, an image is captured of the food product in the visible spectrum by on-line vision equipment, multivariate image analysis is performed on the image via an algorithm programmed onto a field programmable gate array to determine if a defect exists, a signal is sent to downstream sorting equipment, and the sorting equipment then rejects those food products that contain defects.

13 Claims, 3 Drawing Sheets

U.S. PATENT DOCUMENTS

| | | |
|---|---|---|
| 3,305,366 A | 2/1967 | Sutton |
| 3,359,123 A | 12/1967 | Katucki |
| 3,365,301 A | 1/1968 | Lipoma |
| 3,369,908 A | 2/1968 | Gonzalez |
| 3,370,627 A | 2/1968 | Willard |
| 3,404,986 A | 10/1968 | Wimmer |
| 3,436,229 A | 4/1969 | Simpson |
| 3,460,162 A | 8/1969 | Sijbring |
| 3,545,979 A | 12/1970 | Ghafoori |
| 3,578,463 A | 5/1971 | Smith |
| 3,608,728 A | 9/1971 | Trimble |
| 3,620,925 A | 11/1971 | Mochizuki |
| 3,627,535 A | 12/1971 | Davidson |
| 3,634,095 A | 1/1972 | Willard |
| 3,652,402 A | 3/1972 | Chibata |
| 3,687,679 A | 8/1972 | Sijbring |
| 3,690,895 A | 9/1972 | Amadon |
| 3,725,087 A | 4/1973 | Miller |
| 3,773,624 A | 11/1973 | Wagner |
| 3,782,973 A | 1/1974 | Pittet |
| 3,812,775 A | 5/1974 | Sijbring |
| 3,849,582 A | 11/1974 | Blagdon |
| 3,851,572 A | 12/1974 | Lazzarini |
| 3,870,809 A | 3/1975 | Green |
| 3,914,436 A | 10/1975 | Nakadai |
| 3,917,866 A | 11/1975 | Purves |
| 3,925,568 A | 12/1975 | Rao |
| 3,987,210 A | 10/1976 | Cremer |
| 3,997,684 A | 12/1976 | Willard |
| 3,998,975 A | 12/1976 | Liepa |
| 4,005,221 A | 1/1977 | Craig |
| 4,073,952 A | 2/1978 | Standing |
| 4,084,008 A | 4/1978 | Yueh |
| 4,122,198 A | 10/1978 | Wisdom |
| 4,124,727 A | 11/1978 | Rockland |
| 4,136,208 A | 1/1979 | Light |
| 4,140,801 A | 2/1979 | Hilton |
| 4,167,137 A | 9/1979 | van Remmen |
| 4,192,773 A | 3/1980 | Yoshikawa |
| 4,199,612 A | 4/1980 | Fragas |
| 4,210,594 A | 7/1980 | Logan |
| 4,251,895 A | 2/1981 | Caridis |
| 4,272,554 A | 6/1981 | Schroeder |
| 4,277,510 A | 7/1981 | Wicklund |
| 4,312,892 A | 1/1982 | Rubio |
| 4,317,742 A | 3/1982 | Yamaji |
| 4,366,749 A | 1/1983 | Caridis |
| 4,394,398 A | 7/1983 | Wilson |
| 4,418,088 A | 11/1983 | Cantenot |
| 4,461,832 A | 7/1984 | Tschang |
| 4,537,786 A | 8/1985 | Bernard |
| 4,555,409 A | 11/1985 | Hart |
| 4,582,927 A | 4/1986 | Fulcher |
| 4,594,260 A | 6/1986 | Vaquerio |
| 4,595,597 A | 6/1986 | Lenchin |
| 4,645,679 A | 2/1987 | Lee |
| 4,673,581 A | 6/1987 | Fulcher |
| 4,706,556 A | 11/1987 | Wallace |
| 4,721,625 A | 1/1988 | Lee |
| 4,749,579 A | 6/1988 | Haydock |
| 4,751,093 A | 6/1988 | Hong |
| 4,756,916 A | 7/1988 | Dreher |
| 4,806,377 A | 2/1989 | Ellis |
| 4,844,930 A | 7/1989 | Mottur |
| 4,844,931 A | 7/1989 | Webb |
| 4,863,750 A | 9/1989 | Pawlak |
| 4,884,780 A | 12/1989 | Ohashi |
| 4,889,733 A | 12/1989 | Willard |
| 4,900,576 A | 2/1990 | Bonnett |
| 4,917,909 A | 4/1990 | Prosise |
| 4,931,296 A | 6/1990 | Shanbhag |
| 4,933,199 A | 6/1990 | Neel |
| 4,937,085 A | 6/1990 | Cherry |
| 4,963,373 A | 10/1990 | Fan |
| 4,966,782 A | 10/1990 | Heidolph |
| 4,971,813 A | 11/1990 | Strobel |
| 4,978,684 A | 12/1990 | Cerami |
| 4,985,269 A | 1/1991 | Irvin |
| 5,002,784 A | 3/1991 | Pare |
| 5,009,903 A | 4/1991 | deFigueiredo |
| 5,035,904 A | 7/1991 | Huang |
| 5,045,335 A | 9/1991 | DeRooij |
| 5,071,661 A | 12/1991 | Stubbs |
| 5,087,467 A | 2/1992 | Schwank |
| 5,126,153 A | 6/1992 | Beck |
| 5,134,263 A | 7/1992 | Smith |
| 5,137,740 A | 8/1992 | Benson |
| 5,167,975 A | 12/1992 | Tsurumaki |
| 5,171,600 A | 12/1992 | Young |
| 5,176,933 A | 1/1993 | Fulcher |
| 5,196,225 A | 3/1993 | Lush |
| 5,232,721 A | 8/1993 | Polansky |
| 5,279,840 A | 1/1994 | Baisier |
| 5,292,542 A | 3/1994 | Beck |
| 5,298,274 A | 3/1994 | Khalsa |
| 5,356,646 A | 10/1994 | Simic-Glavaski |
| 5,362,511 A | 11/1994 | Villagran |
| 5,368,879 A | 11/1994 | White |
| 5,370,898 A | 12/1994 | Zussman |
| 5,389,389 A | 2/1995 | Beck |
| 5,391,384 A | 2/1995 | Mazza |
| 5,391,385 A | 2/1995 | Seybold |
| 5,393,543 A | 2/1995 | Laufer |
| 5,394,790 A | 3/1995 | Smith |
| 5,441,758 A | 8/1995 | Lewis |
| 5,447,742 A | 9/1995 | Malvido |
| 5,458,903 A | 10/1995 | Colson |
| 5,464,642 A | 11/1995 | Villagran |
| 5,464,643 A | 11/1995 | Lodge |
| 5,505,978 A | 4/1996 | Roy |
| 5,514,387 A | 5/1996 | Zimmerman |
| 5,534,280 A | 7/1996 | Welch |
| 5,554,405 A | 9/1996 | Fazzolare |
| 5,558,886 A | 9/1996 | Martinez-Bustos |
| 5,580,598 A | 12/1996 | Benson |
| 5,589,213 A | 12/1996 | Desai |
| 5,603,972 A | 2/1997 | McFarland |
| 5,603,973 A | 2/1997 | Benson |
| 5,620,727 A | 4/1997 | Gerrish |
| 5,676,042 A | 10/1997 | Sakuma |
| 5,690,982 A | 11/1997 | Fazzolare |
| 5,695,804 A | 12/1997 | Hnat |
| 5,707,671 A | 1/1998 | Beck |
| 5,747,084 A | 5/1998 | Cochran |
| 5,776,531 A | 7/1998 | Aasman |
| 5,792,499 A | 8/1998 | Atwell |
| 5,846,589 A | 12/1998 | Baker |
| 5,858,429 A | 1/1999 | Wallace |
| 5,858,431 A | 1/1999 | Wiedersatz |
| 5,887,073 A | 3/1999 | Fazzari |
| 5,919,691 A | 7/1999 | Schulein |
| 5,945,146 A | 8/1999 | Twinam |
| 5,947,010 A | 9/1999 | Barry |
| 5,972,367 A | 10/1999 | Inoue |
| 5,972,397 A | 10/1999 | Durance |
| 6,001,409 A | 12/1999 | Gimmler |
| 6,016,096 A | 1/2000 | Barnes |
| 6,025,011 A | 2/2000 | Wilkinson |
| 6,033,707 A | 3/2000 | Lanner |
| 6,039,997 A | 3/2000 | Bangs |
| 6,066,353 A | 5/2000 | Martines-Serna Villagran et al. |
| 6,068,872 A | 5/2000 | Hashiguchi |
| 6,068,873 A | 5/2000 | Delrue |
| RE36,785 E | 7/2000 | Colson |
| 6,139,884 A | 10/2000 | Shifferaw |
| 6,159,530 A | 12/2000 | Christiansen |
| 6,207,204 B1 | 3/2001 | Christiansen |
| 6,210,720 B1 | 4/2001 | Leusner |
| 6,227,421 B1 | 5/2001 | Richard |
| 6,287,672 B1 | 9/2001 | Fields |
| 6,290,999 B1 | 9/2001 | Gerrish |
| 6,299,914 B1 | 10/2001 | Christiansen |
| 6,335,048 B1 | 1/2002 | Swarvar |
| 6,358,544 B1 | 3/2002 | Henry, Jr. |
| 6,383,533 B1 | 5/2002 | Soeda |
| 6,419,965 B1 | 7/2002 | Douaire |
| 6,436,458 B2 | 8/2002 | Kuechle |

| | | |
|---|---|---|
| 6,521,871 B1 | 2/2003 | Shelton |
| 6,528,768 B1 | 3/2003 | Simic-Glavaski |
| 6,531,174 B2 | 3/2003 | Barrett et al. |
| 6,558,730 B1 | 5/2003 | Gisaw |
| 6,599,547 B1 | 7/2003 | Villagran |
| 6,602,533 B1 | 8/2003 | Smith |
| 6,607,777 B1 | 8/2003 | Walsh |
| 6,638,554 B1 | 10/2003 | Rubio |
| 6,638,558 B2 | 10/2003 | Brubacher |
| 6,716,462 B2 | 4/2004 | Prosise |
| 6,770,469 B2 | 8/2004 | Yamaguchi |
| 6,778,887 B2 | 8/2004 | Britton |
| 6,828,527 B2 | 12/2004 | Simic-Glavaski |
| 6,872,417 B1 | 3/2005 | Freudenrich |
| 6,896,528 B2 | 5/2005 | Kubota |
| 6,929,812 B2 | 8/2005 | Van Der Doe |
| 6,989,167 B2 | 1/2006 | Howie |
| 7,037,540 B2 | 5/2006 | Elder |
| 7,122,719 B2 | 10/2006 | Hakimi |
| 7,169,417 B2 | 1/2007 | Lang et al. |
| 7,189,422 B2 | 3/2007 | Howie |
| 7,190,813 B2 * | 3/2007 | Daley et al. .................. 382/110 |
| 7,220,440 B2 | 5/2007 | Dria |
| 7,267,834 B2 | 9/2007 | Elder |
| 7,291,380 B2 | 11/2007 | Nyholm |
| 7,393,550 B2 | 7/2008 | Barry |
| 7,514,113 B2 | 4/2009 | Zyzak |
| 7,524,519 B2 | 4/2009 | Zyzak |
| 7,527,815 B2 | 5/2009 | Teras |
| 7,534,934 B2 | 5/2009 | Rommens |
| 2002/0018838 A1 | 2/2002 | Zimmerman |
| 2002/0025367 A1 | 2/2002 | Koehler |
| 2002/0129713 A1 | 9/2002 | Caridis |
| 2003/0049359 A1 | 3/2003 | Kulkarni |
| 2003/0183092 A1 | 10/2003 | Barber |
| 2003/0198725 A1 | 10/2003 | Cardenas |
| 2003/0219518 A1 | 11/2003 | Li |
| 2004/0047973 A1 | 3/2004 | Bourhis |
| 2004/0086597 A1 | 5/2004 | Awad |
| 2004/0101607 A1 | 5/2004 | Zyzak |
| 2004/0105929 A1 | 6/2004 | Tomoda |
| 2004/0109926 A1 | 6/2004 | Tomoda |
| 2004/0115321 A1 | 6/2004 | Tricoit |
| 2004/0126469 A1 | 7/2004 | Tomoda |
| 2004/0131737 A1 | 7/2004 | Tomoda |
| 2004/0180125 A1 | 9/2004 | Plank |
| 2004/0180129 A1 | 9/2004 | Plank |
| 2004/0197012 A1 * | 10/2004 | Bourg et al. .................. 382/110 |
| 2004/0224066 A1 | 11/2004 | Lindsay |
| 2005/0064084 A1 | 3/2005 | Elder |
| 2005/0068535 A1 | 3/2005 | Bond |
| 2005/0074538 A1 | 4/2005 | Elder |
| 2005/0079254 A1 | 4/2005 | Corrigan |
| 2005/0118322 A1 | 6/2005 | Elder |
| 2005/0152811 A1 | 7/2005 | Taylor |
| 2005/0196504 A1 | 9/2005 | Finley |
| 2005/0214411 A1 | 9/2005 | Lindsay |
| 2006/0019007 A1 | 1/2006 | Baas |
| 2006/0088633 A1 | 4/2006 | Barber |
| 2006/0110503 A1 | 5/2006 | Bates |
| 2006/0127534 A1 | 6/2006 | Elder |
| 2006/0193964 A1 | 8/2006 | Eckhoff |
| 2006/0210693 A1 | 9/2006 | Oftring |
| 2006/0216376 A1 | 9/2006 | Milici |
| 2006/0216388 A1 | 9/2006 | Christensen |
| 2007/0042080 A1 | 2/2007 | Plomp |
| 2007/0087101 A1 | 4/2007 | Gusek |
| 2007/0141225 A1 | 6/2007 | Elder |
| 2007/0141226 A1 | 6/2007 | Elder |
| 2007/0141227 A1 | 6/2007 | Boudreaux |
| 2007/0148318 A1 | 6/2007 | Rubio |
| 2007/0166439 A1 | 7/2007 | Soe |
| 2007/0178219 A1 | 8/2007 | Boudreaux |
| 2007/0184175 A1 | 8/2007 | Rubio |
| 2007/0196556 A1 | 8/2007 | Van Der Meer |
| 2007/0281062 A1 | 12/2007 | Bourg |
| 2007/0292589 A1 | 12/2007 | Elder |
| 2008/0003340 A1 | 1/2008 | Karwowski |
| 2008/0008780 A1 | 1/2008 | Streekstra |
| 2008/0101657 A1 | 5/2008 | Durkin |
| 2008/0138480 A1 | 6/2008 | Bows |
| 2008/0144880 A1 | 6/2008 | DeLuca |
| 2008/0166450 A1 | 7/2008 | Corrigan |
| 2008/0166452 A1 | 7/2008 | Corrigan |
| 2008/0253648 A1 | 10/2008 | Mulder |
| 2008/0279994 A1 * | 11/2008 | Cantley et al. ................. 426/233 |
| 2008/0299273 A1 | 12/2008 | Bhaskar |
| 2009/0047725 A1 | 2/2009 | Elder |
| 2009/0074915 A1 | 3/2009 | Hendriksen |
| 2009/0098265 A1 | 4/2009 | Kock |
| 2009/0191310 A1 | 7/2009 | Zyzak |
| 2010/0040729 A1 | 2/2010 | Sahagian |
| 2010/0040750 A1 | 2/2010 | Assaad |
| 2010/0051419 A1 | 3/2010 | Desai |
| 2010/0055259 A1 | 3/2010 | Bourg |
| 2010/0062123 A1 | 3/2010 | Anderson |
| 2010/0112177 A1 | 5/2010 | Bourg, Jr. |
| 2010/0143540 A1 | 6/2010 | Bhaskar |
| 2010/0255167 A1 | 10/2010 | Bourg |

FOREIGN PATENT DOCUMENTS

| | | |
|---|---|---|
| DE | 2743230 A1 | 4/1979 |
| EP | 113940 A1 | 7/1984 |
| EP | 1419702 A1 | 5/2004 |
| EP | 1419703 A1 | 5/2004 |
| ES | 2019044 | 2/1990 |
| FR | 874453 | 8/1942 |
| GB | 156905 | 1/1921 |
| GB | 1132296 | 10/1968 |
| GB | 1519049 | 7/1978 |
| GB | 335214 | 9/1980 |
| JP | 68006927 | 9/1965 |
| JP | 70009815 | 10/1966 |
| JP | 57100179 | 12/1980 |
| JP | 62048351 A | 3/1987 |
| JP | 4104753 | 4/1992 |
| JP | 6030782 A | 2/1994 |
| JP | 06169713 | 6/1994 |
| JP | 05123126 | 5/1998 |
| JP | 10136883 | 5/1998 |
| JP | 11056280 | 3/1999 |
| JP | 11178536 | 7/1999 |
| JP | 2004180563 | 7/2004 |
| JP | 2004-313183 | 11/2004 |
| JP | 2004313183 | 11/2004 |
| JP | 2005278448 | 10/2005 |
| KR | 910006619 B1 | 8/1991 |
| RU | 1822863 | 6/1993 |
| RU | 2048512 | 11/1995 |
| RU | 2078797 | 5/1997 |
| RU | 2140927 | 11/1999 |
| RU | 2216574 | 11/2003 |
| WO | 9601572 | 1/1996 |
| WO | 0004784 | 2/2000 |
| WO | 0191581 | 12/2001 |
| WO | 2004004484 | 1/2004 |
| WO | 2004026043 | 4/2004 |
| WO | 2004028276 | 4/2004 |
| WO | 2004028277 | 4/2004 |
| WO | 2004028278 | 4/2004 |
| WO | 2004032647 | 4/2004 |
| WO | 2004032648 | 4/2004 |
| WO | 2004039174 | 5/2004 |
| WO | 2004040999 | 5/2004 |
| WO | 2004047559 | 6/2004 |
| WO | 2004060078 | 7/2004 |
| WO | 2004080205 | 9/2004 |
| WO | 2006128843 | 12/2006 |
| WO | 2007106996 | 9/2007 |
| WO | 2008061982 | 5/2008 |

OTHER PUBLICATIONS

"Kagaku Dai-jiten (Encyclopedia of Chemistry)," edited by Ohki Michinori, et al., 1989, pp. 317, 96, and 1661 (6 pages).

"Shokuhin Tenkabutsu Binran (List of Food Additives)," 1964, p. 249 (2 pages).

Stark, Jeffrey C., et al., "Tuber Quality" date unknown, found at http://www.cals.uidaho.edu/potato/PotatoProductionSystems/Topics/TuberQuality.pdf 15 pages.

Weaver, M.L., et al., "Sugar-End in Russet Burbank Potatoes," American Journal of Potato Research, 1972, vol. 49, No. 10, pp. 376-382.

Abdel-Kader, Zakia M., "Effect of blanching on the diffusion of glucose from potatoes" (Abstract), Wiley InterScience Journals: Nahrung / Food vol. 36, Iss. 1, 1992, 1 page.

Abstracts of literature search, "Pathway from Asparagine to Acrylamide," 17 pages.

Alternative Medicine Review "Glutathione, Reduced (GSH)" vol. 6, No. 6, 2001, pp. 601-607.

Amrein, Thomas, "Influence of Thermal Processing Conditions on Acrylamide Generation and Browning in a Potato Model System," J. Agric. Food Chem. 2006, 54, pp. 5910-5916.

Ashoor, S.H. & Zent, J.B., "Maillard Browning of Common Amino Acids and Sugars," (Abstract), Wiley InterScience Journals: J. Food Science, vol. 49, Issue 4, Jul. 1984, 2 pages.

Associated Press Washington—"Habrian descubierto el origen de sustancia cancerigena en las papas fritas," Sep. 30, 2002, 2 pages.

Becalski, Adam, et al., "Acrylamide in Foods: Occurrence, Sources, and Modeling," J. Agric. Food Chemistry, 2003, vol. 51, pp. 802-808.

Becalski, Adam, et al., "Acrylamide in French Fries: Influence of Free Amino Acids and Sugars," (Abstract), J. Agric. Food Chem. 52 (12), May 22, 2004, 1 page.

Bosset, Dr. Jacques Olivier, et al. "Mitteilungen aus Lebensmitteluntersuchung und Hygiene" Jun. 2002, vol. 93, Offizielles Organ der Schweizerischen Gesellschaft fur Lebensmittel-und Umweltchemie und der Schweizerischen Gesellschaft fur Lebensmittelhygien(79 pages).

Brathen, Erland, et al., "Addition of Glycine Reduces the Content of Acrylamide in Cereal and Potato Products," J. Agric. Food Chem. 2005, vol. 53, pp. 3259-3264.

CBC News CBC.CA "Food sector told to cut down on toxins in chips, fries" Sep. 19, 2002, 2 pages.

CBC News CBC.CA "Scientists find route for toxin to form in fried, baked foods," Sep. 30, 2002, 3 pages.

CBC News CBC.CA "Some acrylamide with your fries?" Jan. 14, 2003, 6 pages.

Center for Science in the Public Interest article "New Tests Confirm Acrylamide in American Foods," found at http://www.cspinet.org/new/200206251.html, Jun. 25, 2002, 2 pages.

Centre for Molecular and Biomolecular Informatics article "An Amino Acid Bedtime Story" found at http://www.cmbi.kun.nl.gvteach/HAN/alg/infopages/bedtime.html, material from Friedli Enterprises, Gert Vriend, Apr. 18, 2000, 4 pages.

chemhelper.com Home Page for Frostburg State University—Organic Chemistry Help, article "Nucleophilic Addition to Carbonyl Groups" found at http://www.chemhelper.com/nucadd.html, 2000 (3 pages).

Claeys, Wendie L., et al. "Quantifying the formation of carcinogens during food processing: acrylamide," Trends in Food Science & Technology 16 (2005), pp. 181-193.

Database WPI Week 199329 Derwent Publications Ltd., London, GB; AN 1993-234163 XP002473734 & SU 1 750 586 A1 (Interbios Res Assoc) Jul. 30, 1992, 1 page.

Database WPI Week 199805 Thomson Scientific, London, GB; AN 1998-042903 XP002503379, Dec. 4, 1996, 1 page.

de Barber, C. Benedito de, et al. "Reversed-Phase High-Performance Liquid Chromatography Analysis of Changes in Free Amino Acids During Wheat Bread Dough Fermentation" Cereal Chemistry, Feb. 26, 1989, vol. 66, No. 4, pp. 283-288.

de Meulenaer, Bruno, et al., "Comparison of Potato Varieties Between Seasons and Their Potential for Acrylamide Formation," J. Science Food Agric., vol. 88, 2008, pp. 313-318.

de Vleeschouwer, Kristel, et al., "Impact of pH on the Kinetics of Acrylamide Formation/Elimination Reactions in Model Systems," J. Agric. Food Chem. vol. 54, 2006, pp. 7847-7855.

de Wilde, Tineke, et al., "Influence of Fertilization on Acrylamide Formation during Frying of Potatoes Harvested in 2003," J. Agric. Food Chem., 2006, vol. 54, pp. 404-408.

Dunlop, Patricia C., et al. "Nitrogen Catabolite Repression of Asparaginase II in *Saccharomyces cerevisiae*" J. Bacteriology, Jul. 1980, vol. 143, No. 1, pp. 422-426.

El Pais.com, "Hallada la reaccion quimica que produce la acrilamida en las frituras," Jul. 15, 2009, 1 page.

European Commission—Health and Consumer Protection Directorate-General, "Opinion of the Scientific Committee on Food on new findings regarding the presence of acrylamide in food," Jul. 3, 2002, 16 pages.

European Food Safety Authority, Report of "Workshop on Acrylamide Formation in Food," Nov. 17, 2003, Brussels, 22 pages.

"FAO/WHO Joint Consultation on the Health Implications of Acrylamide in Food" Summary Report, Geneva, Switzerland, Jun. 25-27, 2002, 12 pages.

Food Safety Consultations "Health Implications of Acrylamide in Food" Report of a Joint FAO/WHO Consultation, Geneva, Switzerland, Jun. 25-27, 2002, 38 pages.

Joint FAO/WHO Expert Commission on Food Additives, 64th Meeting, Rome, Feb. 8-17, 2005, 47 pages.

Fan, Xuetong, et al. "Effectiveness of Ionizing Radiation in Reducing Furan and Acrylamide Levels in Foods" J. Agric. Food Chem. 2006, 54, pp. 8266-8270.

Fiselier, K., et al., "Brown potato Croquettes Low in Acrylamide by Coating with Egg/Breadcrumbs," Eur. Food Res. Technol. (2004) 219:111-115.

Fiselier, Katell, et al., "Higher Acrylamide Contents in French Fries Prepared from "Fresh" Prefabricates," Eur. Food Res. Technol. (2005) 221:376-381.

Food Standards Agency, "Study of Acrylamide in Food," May 17, 2002, 7 pages.

Francis, Frederick J., "Encyclopedia of Food Science and Technology," 2nd ed., 2000, pp. 2160-2161.

Freshfields Bruckhaus Deringer "Acrylamide in food—The approach of regulators across Europe" Feb. 2003 (20 pages).

Friedman, Mendel, et al., "Browning prevention in fresh and dehydrated potatoes by SH-containing amino acids," Food Additives and Contaminants, 1992, vol. 9, No. 5, pp. 499-503.

Friedman, Mendel, "Chemistry, BioChemistry, and Safety of Acrylamide. A Review," J. Agric. Food Chem., Jul. 3, 2003, vol. 51 (16), pp. 4504-4526.

Friedman, Mendel, et al., "Inhibition of Browning by Sulfur Amino Acids. 1. Heated Amino Acid-Glucose Systems," J. Agric. Food Chem., 1990, 38, pp. 1641-1647.

Friedman, Mendel "The Impact of the Maillard Reaction on the Nutritional Value of Food Proteins" Ch. 6 from The Maillard Reaction: Consequences for the Chemical and Life Sciences, Ikan, Raphael (ed.), 1996, 24 pages.

Garayo, Jagoba, et al. "Vacuum frying of potato chips" J. Food Engineering 55 (2002), pp. 181-191.

Gertz, Christian, et al. "Analysis of acrylamide and mechanisms of its formation in deep-fried products" Eur. J. Lipid Sci. Technol. 104 (2002), pp. 762-771.

Gokmen, Vural, et al., "Acrylamide formation is prevented by divalent cations during the Maillard reaction," Food Chemistry (2006) doi: 10.1016/j.foodchem.2006.08.011, 8 pages.

Granda, Claudia, et al., "Effect of Raw Potato Composition on Acrylamide Formation in Potato Chips," J. Food Science vol. 70, Nr. 9, Nov. 16, 2005, pp. E519-E525.

Granda, Claudia, et al. "Kinetics of Acrylamide Formation During Traditional and Vacuum Frying of Potato Chips" J. Food Process Engineering 28 (2005), pp. 478-493.

Granda, C., et al. "Reduction of Acrylamide Formation in Potato Chips by Low-temperature Vacuum Frying", J. Food Science, vol. 69, Nr. 8, Oct. 7, 2004, pp. E405-E411.

Grivas, Prof. Spiros, et al. "Acrylamide in Food—Mechanisms of Formation and Influencing Factors During Heating of Foods", Report from Swedish Scientific Expert Committee, Apr. 24, 2002 (22 pages).

Harmony House Foods, Inc., http://web.archive.org/web/20050425210612/www.harmonyhousefoods.com/slicedpotato.html, Apr. 25, 2005, 2 pages.

Harrison, Karl "Amino Acids and Proteins" found at http://www.chem.ox.ac.uk/mom/amino_acids/introduction.html, 1996 (2 pages).

Harrison, Karl "Molecules of the Month" found at http://www.chem.ox.ac.uk/mom/, 1996 (1 page).
Dobarganes, Carmen, et al., "Interactions between fat and food during deep-frying," Eur. J. Lipid Sci. Tech. 2000, vol. 102, pp. 521-528.
Erickson, Michael D., ed., Book entitled "Deep Frying—Chemistry, Nutrition and Practical Applications," 2d edition, pp. 262, 263, 274, 275.
Farid, M.M., et al., "The analysis of heat and mass transfer during frying of food using a moving boundary solution procedure," Heat and Mass Transfer, vol. 34, 1998, pp. 69-77.
Fleck, Fiona, "Experts launch action on acrylamide in staple foods," British Medical Journal, Jul. 20, 2002, p. 120.
Jackson, Lauren, "Formation of acrylamide in food," US FDA Centre for Food Safety and Applied Nutrition, National Centre for Food Safety and Technology, Summit—Argo, IL, Dec. 4-5, 2002 presentation, 32 pages.
Lotfi, Ehsan, et al. "A new approach for automatic quality control of fried potatoes using machine learning," Islamic Azad University, Mashad Branch, Ferdowsi University of Mashad, Khorasan Research Center for Technology Development, Mar. 11, 2009, 4 pages.
Pedreschi, Franco, et al. "Acrylamide content and color development in fried potato strips," ScienceDirect Journal of Food Engineering 39 (2006) pp. 40-46.
Research Disclosure 15172, New process for the manufacture of potato-chips from different types of potatoes (not selected), Nov. 1976, 1 page.
Talburt & Smith (eds.), Potato Processing 4th Ed. 1987, "Improving the Color of Potato Chips," pp. 406-413.
Tareke, E., et al., "Acrylamide: A Cooking Carcinogen?" Chem. Res. Toxicol. 2000, vol. 13, pp. 517-522, Published on Web May 27, 2000 (6 pages).
Standard Electrode Potentials, http://www.benjamin-mills.com/chemistry/ecells.htm (2 pages).
AFSSA, French Food Safety Agency, "Acrylamide: Information Point," Jul. 24, 2002 (11 pages).
NFRI Report, published Jul. 1, 2004, Report on the symposium named "Chemistry and Safety of Acrylamide in Food" held by the Agricultural and Food Chemistry Division of the American Chemical Society held on Mar. 28-31, 2004 in Anaheim, CA, USA, published by the National Food Research Institute (NFRI) of the National Agricultural and Food Research Organization of Japan (NARO), available at http://oasys2.confex.com/acs/227nm/techprogram/D941.HTM.
Summary Report of "2004 Acrylamide in Food Workshop: Update—Scientific Issues, Uncertainties, and Research Strategies," held on Apr. 13-15, 2004 in Chicago, IL, USA, published on Aug. 6, 2004, by the National Food Research Institute (NFRI) of the National Agricultural and Food Research Organization of Japan (NARO), available at http://222.jifsan.umd.edu/docs/acry2004.
Martinez-Bustos, F., "Effect of the components of maize on the quality of masa and tortillas during the traditional nixtamalisation process," Journal of the Science of Food and Agriculture, vol. 81, pp. 1455-1462, Aug. 13, 2001, 8 pages.
Sefa-Dedeh, S., "Effect of nixtamalization on the chemical and functional properties of maize," Food Chemistry, vol. 86, pp. 317-324, Aug. 14, 2003, 8 pages.
Health Canada Food & Nutrition "Acrylamide and Food" Dec. 1, 2005 (3 pages).
Health Canada Food & Nutrition "Major pathway of formation of acrylamide in foods and possible approaches to mitigation" Mar. 11, 2005 (2 pages).
Health Canada OCAPI Involving You publication, "Acrylamide and Food," vol. 2, No. 1, Autumn 2002, 2 pages.
Heldman, Dennis R., et al. "Principles of Food Processing" book, 1997, p. 193.
Hughes B.P. "The amino acid composition of potato protein and of cooked potato" British J. of Nutrition, vol. 12, Issue 02, May 1958, pp. 188-195.
Igoe, Robert, Dictionary of Food Ingredients, 4th ed., (Aspen Publishers 2001), pp. 24, 35, 43, 109, and 167.
Institute of Food Science & Technology (UK) "Acrylamide Information and News" found at http://www.ifst.org/acrylmd.htm Sep. 6, 2002, 5 pages.

Ishihara, Katsuyuki, et al. "Examination of Conditions inhibiting the Formation of Acrylamide in the Model System of Fried Potato" Biosci. Biotechnol. Biochem., 70(7), 2006, pp. 1616-1621.
Jacobs, Morris B., Ph.D. "The Chemistry and Technology of Food and Food Products" textbook, 1951, pp. 221-226.
Jespersen, Neil "Chemistry" from Barron's College Review Series on Science, 1997, p. 210.
Jung, M.Y. et al. "A Novel Technique for Limitation of Acrylamide Formation in Fried and Baked Corn Chips and in French Fries", J. Food Science vol. 68, No. 4, 2003, pp. 1287-1290.
Kim, Kyu-Won, et al. "Asparaginase II of *Saccharomyces cerevisiae*" J. Biological Chem. 263 (24), Aug. 25, 1988, pp. 11948-11953.
Kim, Cheong Tae, et al. "Reducing Acrylamide in Fried Snack Products by Adding Amino Acids" J. Food Science vol. 70, Nr. 5, 2005, pp. C354-C358.
Kirk, Raymond E., et al. "Enciclopedia de Tecnologia Quimica" 1962, pp. 986-998.
Kita, Agnieszka, et al. "Effective Ways of Decreasing Acrylamide Content in Potato Crisps During Processing" J. Agric. Food Chem., Oct. 15, 2004, vol. 52, pp. 7011-7016.
Kretovich, V.L. "Plant Biochemistry" book, 1986, pp. 8-11 (English translation).
Lawrence, James E., "Acrylamide in Food" memorandum, Health Canada Food Program publication, Sep. 23, 2002, 1 page.
Low, Mei Yin, et al. "Effect of Citric Acid and Glycine Addition on Acrylamide and Flavor in a Potato Model System" J. Agric. Food Chem. 2006, 54, pp. 5976-5983.
Martin, Fiona L., et al. "Formation of Strecker Aldehydes and Pyrazines in a Fried Potato Model System" J. Agric. Food Chem. 2001, 49, pp. 3885-3892.
May, N.J., et al. "Acrylamide formation in deep-fried potato products and removal of acrylamide precursors" Food Australia 58 (10) Oct. 2006, pp. 488-493.
Mizukami, Yuzo, et al. "Analysis of Acrylamide in Green Tea by Gas Chromatography—Mass Spectrometry" J. Agric. Food Chem. 2006, 54, pp. 7370-7377.
Mottram, Don—The University of Reading, "Acrylamide in Cooked Foods—the Latest 'Food Scare'" 2002 (44 pages).
Mottram, Donald S. "Acrylamide is formed in the Maillard reaction" Nature Magazine, Oct. 3, 2002, found at www.nature.com/nature (1 page).
Murray, Lindsay, "Acrylamide" Center for Clinical Toxicology, Vanderbilt Univ. Med. Ctr., Jul. 1996 found at http://www.inchem.org/documents/pims/chemical/pim652.htm, Jun. 1998 (8 pages).
Mustafa, Arwa, et al. "Factors Influencing Acrylamide Content and Color in Rye Crisp Bread" J. Agric. Food Chem. 2005, 53, pp. 5985-5989.
Neergaard, Lauran "Scientists: Chemical Reaction May Create Carcinogen" Health Zone found at http://www.cjonline.com/stories/093002/hea_carcinogen.shtml, Sep. 30, 2002 (3 pages).
Nielsen, Per Munk "Enzyme Technology for Production of Protein-Based Flavours" Novo Nordisk A/S 1995 (6 pages).
Ou, Shiyi, et al. "Reduction of Acrylamide Formation by Selected Agents in Fried Potato Crisps on Industrial Scale" ScienceDirect, Innovative Food Science and Emerging Technologies 9 (2008) pp. 116-121.
Pedreschi, Franco, et al. "Acrylamide reduction under different pretreatments in French fries" ScienceDirect Journal of Food Engineering 79 (2007) pp. 1287-1294.
Pedreschi, Franco, et al. "Color development and acrylamide content of pre-dried potato chips" ScienceDirect Journal of Food Engineering 79 (2007) pp. 786-793.
Pedreschi, Franco, et al. "Color kinetics and acrylamide formation in NaCl soaked potato chips" ScienceDirect Journal of Food Engineering 79 (2007) pp. 989-997.
Pedreschi, Franco, et al. "Reduction of Acrylamide Formation in Potato Slices During Frying" Lebensm.-Wiss u.-Technol. 37 (2004) pp. 679-685.
Procter & Gamble Press Release Sep. 27, 2002 "Procter & Gamble Makes Significant Advances on Understanding Acrylamide Formation" found at http://biz.yahoo.com/prnews/020927/clf005_1.html (2 pages).

Raloff, Janet, "Hot Spuds: Golden Path to Acrylamide in Food" Science News Online, Oct. 5, 2002, vol., 162 found at http://www.sciencenews.org/20021005/fob5.asp (3 pages).

Rossell, J.B. (ed.) "Frying—Improving Quality" CRC Press, 2001, pp. 198-214 and 306-308.

Rydberg, Per, et al. "Investigations of Factors That Influence the Acrylamide Content of Heated Foodstuffs" J. Agric. Food Chem. 2003, vol. 51, pp. 7012-7018.

Sanders, R.A., et al. "An LC/MS Acrylamide Method and Its Use in Investigating the Role of Asparagine," printout of presentation slides (24 pages).

Segtnan, Vegard H., et al. "Screening of acrylamide contents in potato crisps using process variable settings and near-infrared spectroscopy" Mol. Nutr. Food Res. vol. 50, 2006, pp. 811-817.

Stadler, Richard H., et al. "Acrylamide from Maillard reaction products" Nature Magazine Oct. 3, 2002 found at www.nature.com/nature (2 pages).

Talburt & Smith (eds.), Potato Processing 4th Ed. 1987, Ch. 12 "Dehydrated Mashed Potatoes—Potato Granules," pp. 535-555.

Talburt & Smith (eds.), Potato Processing 4th Ed. 1987, "Improving the Color of Potato Chips," pp. 403-405.

Tareke, Eden, et al., "Analysis of Acrylamide, a Carcinogen Formed in Heated Foodstuffs," J. Agric. Food Chem. pp. A through I.

"Temperature and Heat—Local Materials" Mar. 2003 found at http://web.archive.org/web/20030321105136/http://www.pa.uky.edu/sciworks/xtra/local.htm (3 pages).

U.S. Dept. of Health and Human Services, Public Health Service, National Toxicology Program, "9th Report on Carcinogens Revised Jan. 2001" found at http://win2000.kreatiweb.it/sanitaweb/web/Biblioteca/carcinogens/rahc/acrylamide.pdf (5 pages).

U.S. Dept. of Health & Human Services, U.S. Food and Drug Adm., Center for Food Safety and Applied Nutrition "Exploratory Data on Acrylamide in Foods" Dec. 4, 2002 found at http://www.mindfully.org/food/acrylamide-foods-fda (9 pages).

U.S. Food and Drug Administration Public Meeting "Assessing Acrylamide in the U.S. Food Supply," Sep. 30, 2002 (5 pages).

Viklund, Gunilla A., et al., "Variety and Storage Conditions Affect the Precursor Content and Amount of Acrylamide in Potato Crisps," J. Sci. Food Agric. 2008, vol. 88, pp. 305-312.

Vivanti, Vittorio, et al. "Level of Acrylamide Precursors Asparagine, Fructose, Glucose, and Sucrose in Potatoes Sold at Retail in Italy and in the United States" J. Food Science, vol. 71, Nr. 2, 2006, pp. C81-C85.

Watson, S.A. (ed.), Corn: Chemistry and Technology, American Association of Cereal Chemists, 1987, pp. 410-420.

Webb, Edwin C., "Enzyme Nomenclature 1992," Academic Press, p. 422.

Weisshaar, Rudiger, et al. "Formation of Acrylamide in Heated Potato Products—Model Experiments Pointing to Asparagine as Precursor" Pub. Oct. 3, 2002, Deutsche Lebensmittel-Rundschau 98 Jahrgang, Heft (4 pages).

Williams, J.S.E., "Influence of Variety and Processing Conditons on Acrylamide Levels in Fried Potato Crisps," ScienceDirect Food Chemistry 90 (2005), pp. 875-881.

"Working Group 1: Mechanisms of Formation of Acrylamide in Food" Summary Report (7 pages).

Wulfsberg, Gary, Inorganic Chemistry book, University Science Books, 2000, p. 289.

Yarnell, Amanda, "Acrylamide Mystery Solved," Chemical & Engineering News, Oct. 4, 2002 found at http://pubs.acs.org/cen/today/oct4.html (3 pages).

Yaylayan, Varoujan A., et al., "Why Asparagine Needs Carbohydrates to Generate Acrylamide," J. Agric. Food Chem. 2003, vol. 51, pp. 1753-1757.

Zhang, Yu, et al., "Study on Formation of Acrylamide in Asparagine-Sugar Microwave Heating Systems Using UPLC-MS/MS Analytical Method," ScienceDirect, Food Chemistry 108 (2008), pp. 542-550.

Zyzak David V. et al., "Acrylamide Formation Mechanism in Heated Foods," J. Agric. Food Chem. 2003, vol. 51, pp. 4782-4787.

Zyzak, David, et al. v. Elder, Vincent Allen, et al., Board of Patent Appeals and Interferences, Judgment-Arbitration-Bd.R. 126(f), Apr. 14, 2008, 2 pages.

* cited by examiner

METHOD FOR REAL TIME DETECTION OF DEFECTS IN A FOOD PRODUCT

BACKGROUND OF THE INVENTION

1. Technical Field

This invention relates to the use of multivariate image analysis to detect defects on a production line producing a food product.

2. Description of Related Art

The chemical acrylamide has long been used in its polymer form in industrial applications for water treatment, enhanced oil recovery, papermaking, flocculants, thickeners, ore processing and permanent-press fabrics. Acrylamide precipitates as a white crystalline solid, is odorless, and is highly soluble in water (2155 g/L at 30° C.). Synonyms for acrylamide include 2-propenamide, ethylene carboxamide, acrylic acid amide, vinyl amide, and propenoic acid amide. Acrylamide has a molecular mass of 71.08, a melting point of 84.5° C., and a boiling point of 125° C. at 25 mmHg.

In recent times, a wide variety of foods have tested positive for the presence of acrylamide monomer. Acrylamide has especially been found primarily in carbohydrate food products that have been heated or processed at high temperatures. Examples of foods that have tested positive for acrylamide include coffee, cereals, cookies, potato chips, crackers, french-fried potatoes, breads and rolls, and fried breaded meats. Acrylamide has not been determined to be detrimental to humans, but its presence in food products, especially at elevated levels, is undesirable.

One way to reduce the formation of acrylamide is to thermally process food products to a higher moisture content. However, food products that contain too much moisture have poor organoleptical properties and are undesirable to consumers. It is the objective of the present invention to detect defects, particularly food products having a moisture content above a certain threshold, in a process producing a food product with a higher moisture content.

SUMMARY OF THE INVENTION

One aspect of the present invention is directed towards a method for the real time detection of defects in a food product comprising the steps of capturing an image of a food product in the visible spectrum, performing multivariate image analysis on the image to reveal a data set, and determining whether a defect exists in the food product based on the data set. In one aspect, the invention further comprises removal of food products containing a defect prior to a packaging step. One aspect of the invention comprises adjusting a process variable to reduce the number of manufactured food products that are defective. One aspect of the present invention comprises analyzing and removing the food products for acrylamide defects.

One aspect of the present invention is directed towards a field programmable gate array having an algorithm that transforms a color image of a food product into a data set such as a $t_1$-$t_2$ score space via multivariate image analysis, determines if a defect exists based on the data set, and sends a signal to downstream sorting equipment to reject said defect within about 0.002 seconds.

In one aspect, the present invention is directed towards an apparatus for monitoring a process producing a food product for defects. In one aspect, the apparatus comprises an image capturing device, a computing device capable of storing an algorithm, wherein said algorithm transforms a color image of a food product into a suitable expression of an image matrix via multivariate image analysis, and determines if a defect exists based on a resulting data set.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 3b is a depiction of the corrected image of the defective soft center region superimposed upon the fried potato chips depicted in FIG. 3a;

DETAILED DESCRIPTION

The present invention, in one embodiment, comprises a method for real-time detection of defects in a process producing a food product. The present invention can be used to monitor a process producing a food product and detect food products that contain defects by utilizing multivariate image analysis to differentiate between characteristics of the food product, some of which are defective and some of which are not, that appear similar when viewed in the visible spectrum.

Figure 1:
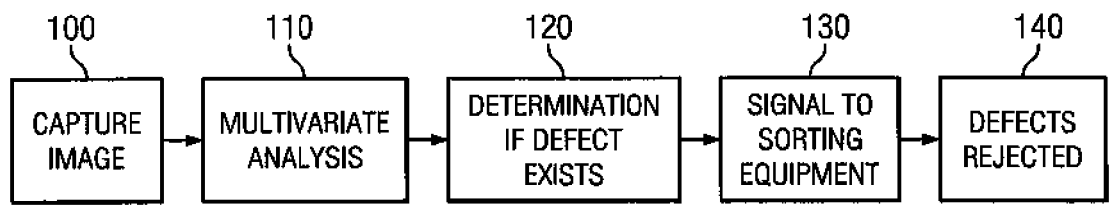
FIG. 1 depicts a general flow chart of a method for detecting defects in a process producing a food product in accordance with one embodiment of the present invention.

Referring now to FIG. 1, an image is captured 100 of the food product in the visible spectrum, which encompasses the wavelength range of 400 nm to 700 nm, by on-line vision equipment such as a digital camera, as the product proceeds down the process line. In one embodiment, the entire width of a conveyor belt is imaged thereby providing maximum inspection and analysis of the surface of the food product. In one embodiment the food is in a monolayered configuration. Bedded food products can be placed into monolayered configuration by transferring bedded food product from a first conveyor belt to a much faster moving second conveyor belt. Multivariate image analysis (hereinafter "MIA") is then performed on the image via an algorithm 110. In one embodiment, the algorithm can be programmed into a field programmable gate array (FPGA), which is a semiconductor device, known in the art, that can be programmed in the field. In one embodiment, an application specific integrated circuit can be used to process the algorithm. The algorithm can be used to reveal a data set, which depicts the location of the product characteristics in the $t_1$-$t_2$ score space or other suitable expression of the image matrix via multivariate image analysis.

Next, it is determined if a defect exists 120 based on the resulting data set. In one embodiment, if a defect is found, a signal 130 can be sent to sorting equipment, such as a bank of independently selected air nozzles, located downstream from the vision equipment, to reject the food product containing the defect. The sorting equipment then rejects those food products that contain defects by deflecting the defective food products from the conveyor carrying the product with a stream of air from an air nozzle prior to a packaging step.

In one embodiment, the invention comprises using the real time measurement of defects to adjust a process variable in the food manufacturing line to lower the percentage of defects in the food products.

One embodiment of the present invention can be explained with reference to a potato chip production line and "soft center" defects that occur in fried potato chips having a moisture content of greater than about 2.5% by weight. A soft center defect occurs when a thermally processed food such as a fried potato chip is not cooked to a moisture content that ensures a crispy texture throughout the food product. Thus, the central region of the food product is relatively soft. Soft centers are problematic because they adversely affect the shelf life of the product by increasing the amount of moisture in the product container and lead to the product becoming stale more rapidly. Further, soft centers affect the texture of the potato chip, which results in decreased consumer satisfaction, and can cause multiple chips to stick together, which results in problems during further processing.

Figure 2:
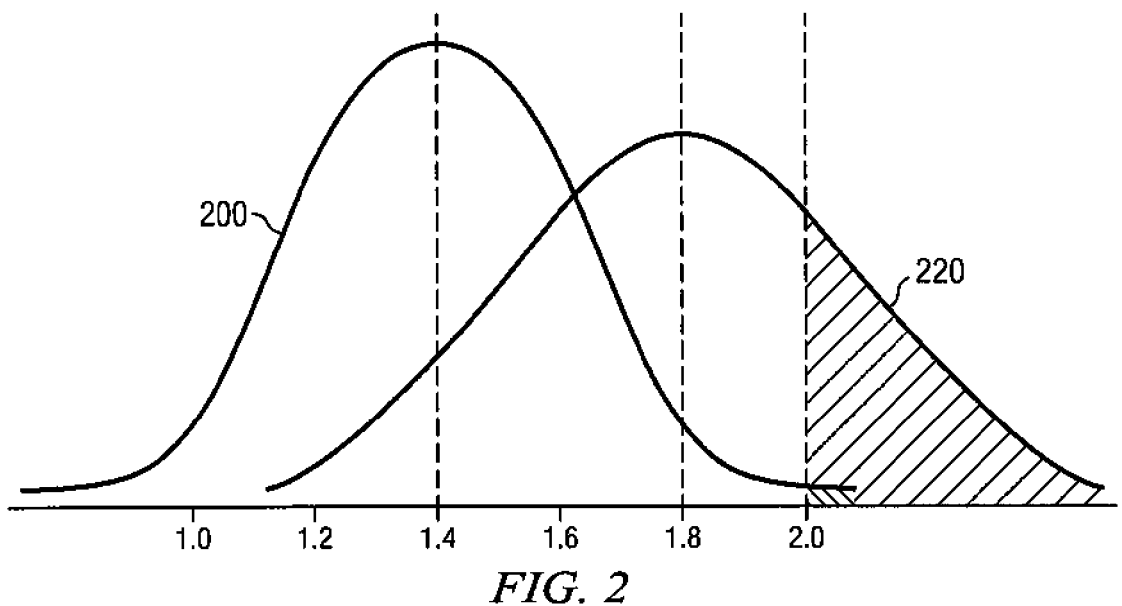
FIG. 2 depicts prophetic moisture content distributions of potato chips.

As foods are thermally processed to higher moisture contents to lower the level of acrylamide in the food, soft center defects become more prevalent. For example, potato chips are typically cooked by frying to a moisture content distribution prophetically depicted by curve 200 in FIG. 2. As shown in FIG. 2, when potato chips are fried to a target moisture content of about 1.4% by weight, very few of the fried potato chips have moisture contents above 2% by weight. However, thermally processing foods to higher moisture contents such as a target moisture content of about 1.8% by weight, to reduce the formation of acrylamide can result in an unintended consequence of producing larger numbers of soft centers, which need to be removed from the product stream prior to packaging. The curve 220 in FIG. 2 represents the prophetic moisture content distribution of a thermally processed potato chip fried to a target moisture content of about 1.8%. As shown by FIG. 2, raising the target moisture content of the potato chips results in a much greater percentage of the chips having a moisture content of more than about 2.0%. Also evident in FIG. 2 is that the prophetic moisture distribution 220 is wider as the target moisture is increased. The reason that the moisture distribution 220 increases is that the lower end of the distribution is further from the constraint of the "bound" moisture content of the finished potato chip. Consequently, an even greater than expected level of soft center defects occurs by raising the target moisture content.

Existing sorting equipment in the production of potato chips based on the visible spectrum sorts out defective chips based on the degree of darkness (e.g. black, brown, green), and size of the observed defect on the chip. However, detecting soft center defects with the existing equipment is difficult because soft centers reflect light differently than other defects because soft center defects emit a white or glossy/shiny wavelength signature. For example, color is sometimes described in an HSI (hue, saturation, intensity) color space. It is difficult to use the HSI colorspace to accurately detect soft centers because the glare or glossy component, which is mostly unrelated to the object's actual saturation and intensity properties, is necessarily measured by the HSI technology. Further complicating matters is the fact that oil-soaked chips, which are not considered defective, also emit a white or glossy wavelength signature and can be erroneously rejected along with the soft centers.

Oil soaked chips are fried food products where the oil is not attached to the starch. Various regions of the fried chip can be oil-soaked. In some embodiments, because chips are analyzed for defects within a relatively short period of time after exiting the fryer, oil can still be on the surface of the fried food if the oil is not yet been imbibed into the food product. Oil soaked chips are not considered defective. Consequently, a need exists for an apparatus and method to monitor a thermally processed food product production line for soft centers, and selectively reject the soft centers without rejecting oil-soaked chips.

While thermally processed fried food products are typically processed to moisture contents of less than 2.5% by weight of the food product, and more preferably less than about 2.0% by weight of the food product, baked goods such as crackers can be thermally processed to higher moisture contents and still be shelf-stable. Consequently, as used herein, a thermally processed food product is defined as a food product having a moisture content of less than about 5% by weight, and more preferably less than about 3.5% by weight. As used herein, the term chip and thermally processed food product are used interchangeably.

One embodiment of the present invention allows soft center defects and oil-soaked chips to be differentiated by performing multivariate image analysis on an image taken in the visible spectrum of the thermally processed food product to construct an algorithm that can be used to identify features, such as soft center defects and oil-soaked areas on the food product.

A color image captured in the visible spectrum is a multivariate image composed of three variables—red, green and blue channels. The color of each pixel in the image has varying intensities of the colors red, green and blue and is characterized by the numerical values (normally integers from 0 to 255) of its red, green and blue channels. A color image can be expressed as a 3-way matrix. Two dimensions represent the x-y spatial coordinates and the third dimension is the color channel. Without considering the spatial coordinates of pixels, the image matrix can be unfolded and expressed as a 2-way matrix.

$$I_{N_{row} \times N_{col} \times 3} \xrightarrow{unfold} I_{N \times 3} = \begin{bmatrix} c_{1,r} & c_{1,g} & c_{1,b} \\ M & M & M \\ c_{i,r} & c_{i,g} & c_{i,b} \\ M & M & M \\ c_{N,r} & c_{N,g} & c_{N,b} \end{bmatrix} = \begin{bmatrix} c_1 \\ M \\ c_i \\ M \\ c_N \end{bmatrix}$$

I is a 3-way image matrix with image size $N_{row} \times N_{col}$. $\overline{I}$ is the unfolded 2-way image matrix. N is the number of pixels in the image, $N = N_{row} \times N_{col}$, $c_{i,r}$, $c_{i,g}$, $c_{i,b}$ (i=1, ..., N) are the intensity values of the red, green and blue channels for pixel i. $c_i$ (i=1, ..., N) is the i-th row vector of I, which represents the color values of pixel i. Different regression methods known in the art, such as Principle Component Analysis (PCA) or Partial Least Squares (PLS), may be used on the 2-way matrix I to obtain a $t_1$-$t_2$ score space.

For example, multi-way Principle Component Analysis can be performed on the multivariate color image to obtain a t1-t2 score space. Multi-way PCA is equivalent to performing PCA on the unfolded 2-way image matrix I.

$$I = \sum_{a=1}^{A} t_a p_a^T$$

where A is the number of principal components, the $t_a$'s are score vectors and the corresponding $p_a$'s are loading vectors.

Because the row dimension of the 2-way image matrix I is very large (equal to 307,200 for a 480×640 image space) and the column dimension is much smaller (equal to 3 for an RGB color image), a kernel algorithm can be used to compute the loading and score vectors. In this algorithm, the kernel matrix ($I^T I$) is first formed (for a set of images, kernel matrix is calculated as $$\sum_k I_k^T I_k),$$

and then singular value decomposition (SVD) is performed on this very low dimension matrix (3×3 for color image) to obtain loading vectors $p_a$ (a=1, . . . , A).

After obtaining loading vectors, the corresponding score vectors to are then computed ta=I pa. Since the first two components normally explain most of the variance, instead of working in original 3-dimensional RGB space, working in the 2-dimensional orthogonal t1-t2 score space allows the images to be more easily interpreted.

Figure 4:
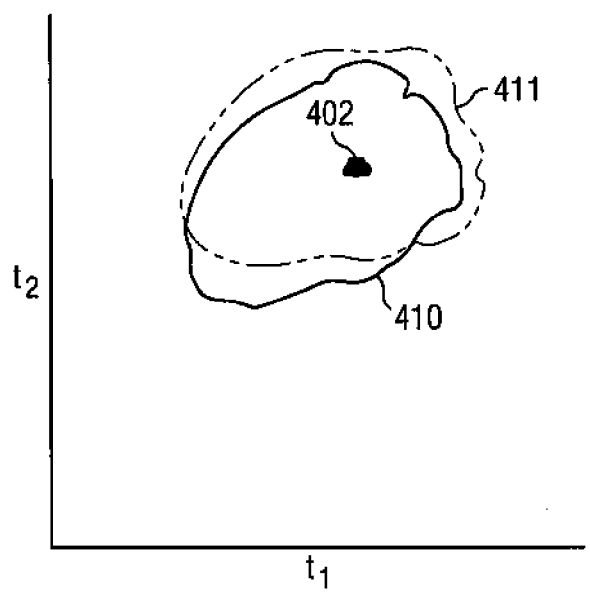
FIG. 4 is a prophetic representation of the color images of two fried potato chips transformed into the $t_1$-$t_2$ score space.
Figure 3A:
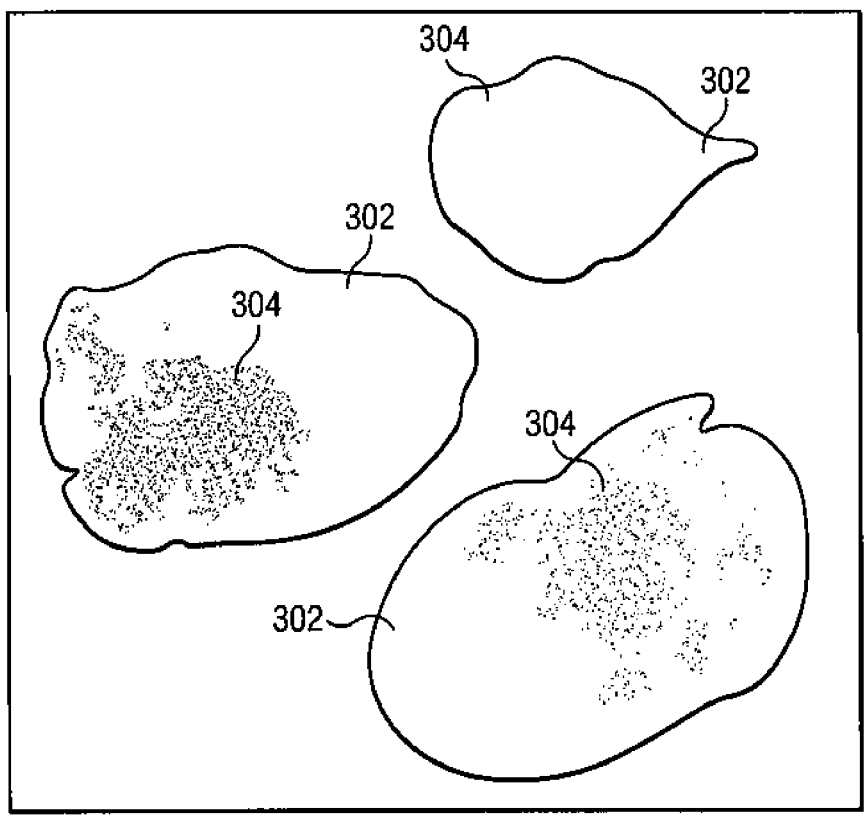
FIG. 3a depicts a plurality of fried potato chips, each chip having a desirable crispy region and a defective soft center region.

FIG. 3a depicts a plurality of fried potato chips, each chip having a desirable, non-defective crispy region 302 and a soft center region 304. The lightly hatched region depicted by numeral 304 necessarily represents a darker color in this drawing than would be indicative of a soft center on an actual color image, and is depicted to show a prophetic soft center region 304. FIG. 4 is a prophetic representation of the color images of two fried potato chips transformed into the $t_1$-$t_2$ score space. Computer software for transforming an image into a $t_1$-$t_2$ score space is known in the art.

To develop the algorithm used to accomplish the multivariate image analysis that correlates the color image of a fried potato chip to determine whether the chip is defective, a multiway PCA is performed on two of the images in FIG. 3a to convert the $t_1$-$t_2$ score space of each potato chip 410 411 depicted in FIG. 4.

Modifications may be made to existing equipment to enable the user to look for white/glossy areas, such as changing the belt material from white to a darker color like blue to allow differentiation between the background/transport belt color and the defect thereby permitting more accurate detection of soft centers. Consequently, in one embodiment, the background color, for example the color of the conveyor belt, is removed from the image in FIG. 3a prior to converting the image of each potato chip into $t_1$-$t_2$ score space. Following removal of the background, the RGB image of the potato chip depicted in FIG. 3a can then be converted into a transformed image 410 411 depicted in FIG. 4. Those having ordinary skill in the art will understand that different food products will produce different $t_1$-$t_2$ score spaces. For example the $t_1$-$t_2$ score space fora tortilla chip will be different than the $t_1$-$t_2$ score space for a potato chip. It should be pointed out that there are other ways to unfold and express the image matrix other than the $t_1$-$t_2$ score space and such expression is provided for purposes of illustration and not limitation.

Next, a mask is created by highlighting an identified defect in the RGB space and observing where the defect falls in the $t_1$-$t_2$ space. A mask 402 is created that highlights the area in the $t_1$-$t_2$ space that is characteristic of the defect, which corresponds to the soft center region identified by numeral 304 in FIG. 3a. In one embodiment, the mask 402 occurs in the same $t_1$-$t_2$ space even though score space of each potato chip 410 411 may encompass different areas on the $t_1$-$t_2$ space.

Figure 3B:
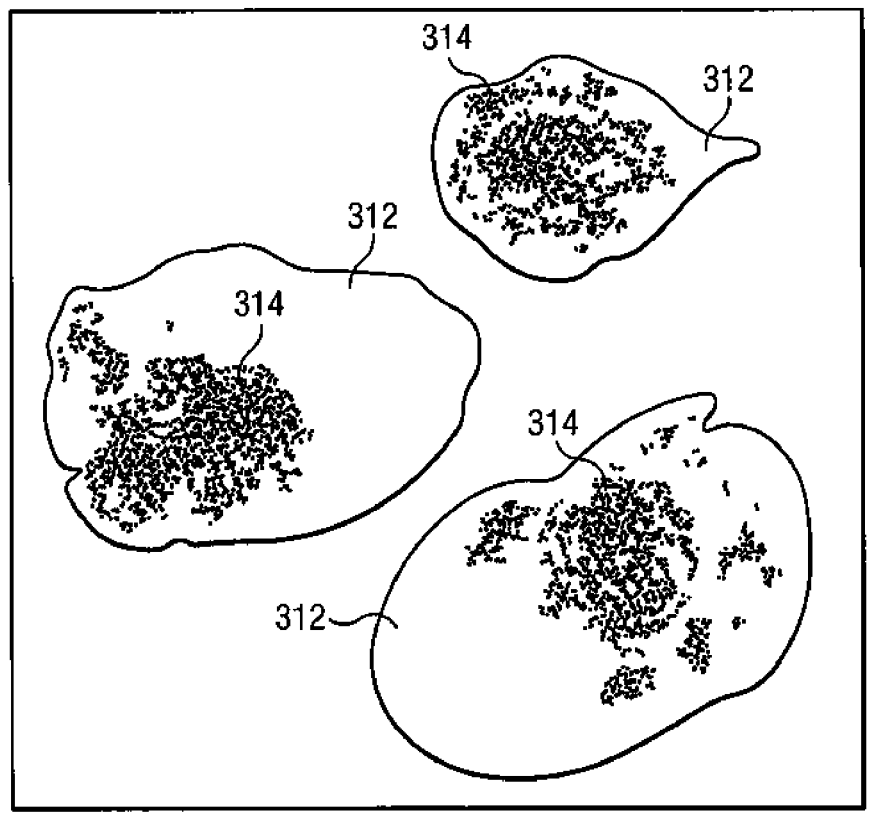

The area comprising the mask 402 in the $t_1$-$t_2$ space is selected and a corrected image is projected back into the RGB space on the potato chip shown in FIG. 3b. Mask areas around the defect region 304 shown in FIG. 3a are, in one embodiment, selected by trial and error until the corrected image mapped back into the RGB space is substantially superimposed upon the defective area 314 of the chip shown in FIG. 3b. In one embodiment, the mask areas around the defect region 304 shown in FIG. 3a can be selected by an automation algorithm that can optimize the mask generation task.

The above process can be repeated to define masks that are correlated with other food product properties including, but not limited to, other defects. For example, potato slices with defects have also been found to be linked with higher levels of acrylamide when fried in hot oil (e.g., fried in oil having an oil temperature of greater than about 280° F.) than potato slices having no potato defects. A potato slice having no defects is a slice having an evenly golden color on its entire surface area after frying. Potato defects are well known to those skilled in the art and such defects include, but are not limited to zebra, dry rot, scab, hollow heart, greening, blackleg, sprouting, bruises, leaf roll and sugar defects. Additional detail on defects found in potatoes, including a listing of such defects, can be found in Information Bulletin 205 titled 'Detection of Potato Tuber, Diseases and Defects' published by the Cornell University Department of Plant Pathology on their website at http://vegetablemdonline.ppath.cornell.edu/factsheets/Pota-to_Detection.htm. This information bulletin is incorporated herein by reference.

Several fried potato slices having various defects were fried to a moisture content below 2% by weight in hot oil and analyzed for levels of acrylamide. The results are provided in the table below.

| Defect | Fried Potato Chip Acrylamide Level (ppb) |
|---|---|
| Zebra | 4435 |
| High Sugar | 2062 |
| Black Leg | 1081 |
| Sprout | 1927 |
| Green | 1816 |
| Bruise | 531 |
| Rot | 1564 |

Sugar defects are not typically removed from product streams prior to packaging. Interestingly, chips having the highest acrylamide levels because of sugar defects have not historically been flagged as consumer defects, because these defects have predominantly light to mid-brownish colors and therefore are not considered unacceptable. Rather, defects such as rot, blackleg, and sprouting which have predominantly black or very dark colors are the types of potato defects most likely to be removed prior to packaging.

As exemplified by the data above, removal of defective fried potato chips from the packaging process can help to substantially reduce the average level of acrylamide in a food product serving. Consequently, in one embodiment of the invention, a food product having an acrylamide defect known to be characteristic of high levels of acrylamide is removed prior to packaging the food products. As used herein, a food product has an acrylamide defect known to be characteristic of a high level of acrylamide if the acrylamide concentration due to the defect is more than twice the level of a non-defective potato slice thermally processed under the same conditions. Thus, a slice having a sugar defect is one that because of higher than normal sugar content will produce a finished potato slice having more than twice the level of acrylamide as a potato slice having a normal sugar content (e.g., chipping potatoes typically have less than 0.05% reducing sugar by weight of a fresh potato) that is thermally processed under the same conditions.

In one embodiment, a mask is created by highlighting a non-defective portion of a chip, such as an oil-soaked region and observing where the defect falls in the RGB space. Mask areas can again be selected by trial and error or by an automated algorithm until the oil-soaked area produces a corrected image that adequately covers the non-defective area of the chip. In this way, a differentiation can be made between the light colored area on the potato chip that is caused by a defective soft center as opposed to a light colored area on the potato chip that corresponds to non-defective oil-soaked chip. Software, such as Proportion, from Prosensus, Inc. can be used to develop the algorithm in the manner discussed above to accomplish the multivariate image analysis that can be used to create the corrected image.

This algorithm can then be programmed into a FPGA to determine, based on the captured image and corresponding dataset calculated from that image, the number, type, and degree of defect pixels within the chip, and establish which chips are defective. FPGA's are known in the art and can, for example, be purchased from Hunt Engineering of Brent Knoll Village, Somerset, England.

Advantageously, the present invention, unlike the prior art, permits one or more defective areas within the chip to be aggregated. In one embodiment, defects most associated with acrylamide can be weighted so that acrylamide defects require less defective area for removal than other defects, such as soft centers, which have relatively low levels of acrylamide. Whether a chip is classed as defective can be determined by one or more pre-determined variables. In one embodiment, a defect exists when the dataset or corrected image reveals that at least about 10% of the imaged food comprises a soft center.

In one embodiment, defective chips are targeted for removal. If a chip has been targeted for removal, the FPGA can calculate the target area, translate the target area to the specific rejection nozzles in the bank of air nozzles downstream, calculate the necessary timing, and communicate the firing sequence to the ejector controller. Sorting equipment such as a Manta high capacity sorter available from Key Technologies of Walla Walla, Wash. can be used.

Figure 5:
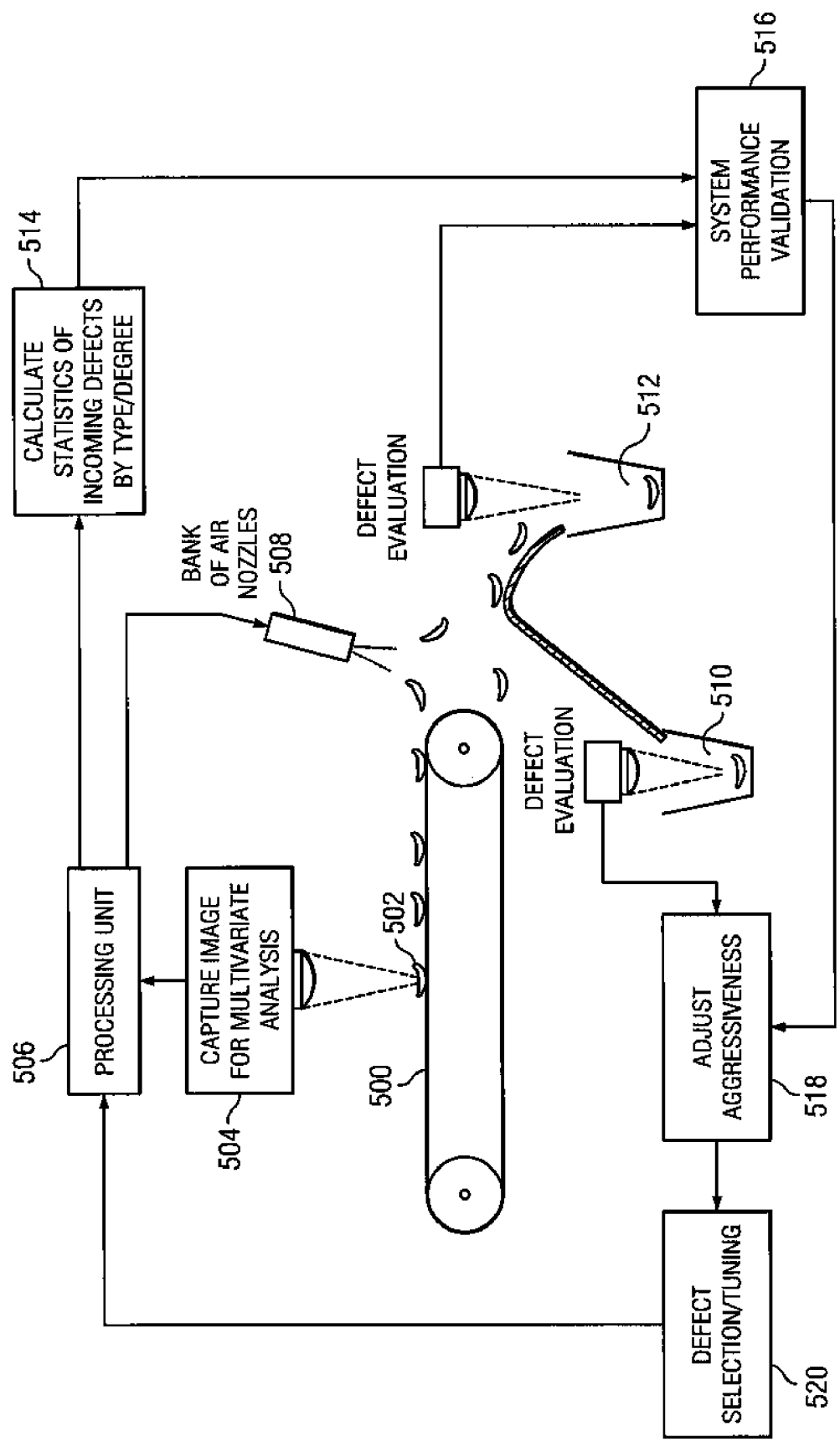
FIG. 5 depicts a schematic representation of one embodiment of the present invention.

FIG. 5 depicts a schematic representation of one embodiment of the present invention. In one embodiment, the bank of independently triggered air nozzles 508, situated about the entire width of the conveyor 502, are located a short distance (e.g., less than about 5 feet and more preferably less than about 3 feet) downstream from the image capturing equipment 504. Therefore, in such embodiment, if the food product 502 is moving along the conveyor at speeds upward of 500 ft/min, the multivariate image analysis and determination of whether a chip is defective must take place very quickly.

To accomplish this, the algorithm can be programmed into the processor 506 that is connected with the vision equipment 504 and sorting equipment 508. A color image of a potato chip 502 can be taken by the vision equipment 504 and sent to the processing unit 506. The processing unit 506 can comprise an FPGA.

The processor 506 applies the algorithm that was developed by methods discussed above to the image, which transforms the color image into a $t_1$-$t_2$ score space or other suitable expression of the image matrix via multivariate image analysis and determines if a defect exists based on the resulting data set. In one embodiment, the resulting dataset is used to superimpose a corrected image in the RGB space onto the food substrate.

In one embodiment, if a defect exists, a signal is sent to the downstream sorting equipment 508 to reject the defective chip. Using FPGA and/or high speed processor array technology 506 allows the process to occur in less than about 0.002 seconds and more preferably in less than about 0.001 seconds to allow actuation of high speed air solenoid valves connected to air nozzles 508 that are selected to remove identified defects from the product stream. Defective chips are routed to a defect stream 510 while the non-defective chip stream 512 is routed to seasoning and/or packaging.

In one embodiment, if a defect exists, a signal can then be used to adjust process variables to adjust the defect levels in a finished food product. For example, the time and temperature of exposure of a food product in the fryer can be optimized so as to reduce, lower and/or minimize the level of defects in the finished food product. For example, the paddle wheel speed can be decreased to permit a longer residence time in the fryer and/or the hot oil temperature can be increased to fry out the soft centers. Other process levels that can be adjusted include, but are not limited to, oil flow rate into the fryer, the oil level in the fryer, the submerger speed, the take out conveyor speed, the inlet oil temperature, and the product feed rate.

In one embodiment, an evaluation of the defect stream 510 and/or non-defect stream 512 occurs to provide additional fine tuning to the process. For example, in one embodiment, the defect stream 510 is measured to ascertain the level of non-defective chips in the defect stream 510. In one embodiment, the non-defect stream 512 is measured to ascertain the level of defective chips in the non-defective stream 512. This information is collected, along with statistics of the incoming defects by type and degree calculated from the processor 506 and used to adjust the algorithm. Such fine tuning can be achieved in one embodiment by observing the shape of the mask in the t1-t2 image and increasing (causing more of the pixels to fit within the definition of a specified defect class) or decreasing (causing less of the pixels to fit within the definition of a specified defect class) the radial distance from the centroid of the mask, 402 shown in FIG. 4.

In one embodiment, the number, type, and degree of defect pixels within each chip in the defective stream 510 and/or the non-defective stream 512 are counted for purposes of statistical analysis 514. In one embodiment, these statistics can be combined with the level of defective chips in the non-defect stream 512 to evaluate the performance 516 of the system. Using the information from the system performance 516, and the level of non-defective food products in the defect stream 510, calculations can be made to adjust the aggressiveness 518 of the tuning as it applies to each individual defect class. For example, as it applies to each individual defect class if a high number of defects are being passed through the system, the tuning action would be to steadily increase the sensitivity of each defect, by class, until an acceptable degree of defect rejection is achieved. On the other hand, if the number of defects in the non-defective stream 512 is within acceptable performance limits, and the number of "good" chips in the reject stream 510 is unacceptably high (meaning that yield is being given up), then the system could be tuned by decreasing the sensitivity or aggressiveness 518 to certain defect classes (the ones that are less egregious in terms of acrylamide) to reduce the number of "good" chips occurring in the reject stream 510.

This information can be used alone or in conjunction with a manual input by an operator to adjust the overall sensitivity 520 of the system. In such embodiment, an operator would have access to an operator input device such as a slide bar or up/down arrow keys, or a "bias" adjustment/numeric input based on any desired scale (e.g. 0-100, +1-10, etc) that would be used to bias the overall system sensitivity to defects. For, example, if the operator wants to increase the allowable defects in the "good" or non-defective stream 512 to increase or decrease by a given percentage, say from 5% to 4%, the operator would be able to make this adjustment manually. In one embodiment, the manual adjustment by an operator would be unavailable to adjust the sensitivity of certain classes of defects, specifically those resulting in increased acrylamide levels, to ensure that rejection of such defects could not be overridden manually by an operator.

Prophetic Example

Potato slices are cooked in a continuous fryer at, for example, a temperature of about 340° F. to about 370° F. for approximately 3 minutes. The cooking step generally reduces the moisture level of the chip to less than 2% by weight. For example, a typical fried potato chip exits the fryer with approximately 1.5% moisture by weight.

The cooked potato chips exit the fryer and proceed along a conveyor at approximately 8 feet per second. A digital camera, positioned above the conveyor, captures a color image of the chip as it proceeds down the conveyor. The image is sent to the processing unit containing the FPGA or processor array with the programmed algorithm. The FPGA or processor array applies the algorithm to transform the color image into a $t_1$-$t_2$ score space. The algorithm then determines if the potato chip is defective based where the chip's characteristics are located in the $t_1$-$t_2$ score space. A mask is created that highlights the area in the $t_1$-$t_2$ score space that is characteristic of the defect. This is done first by highlighting an identified defect in the RGB space and observing where the defect falls in the $t_1$-$t_2$ space. An area around the point in the $t_1$-$t_2$ score space is selected and projected back into the RGB space. Mask areas around the defect region would have been previously identified by trial and error until the area mapped back into the RGB space adequately covers the defective area of the chip. The FPGA signals the sorting equipment, that in one embodiment comprises one or more air nozzles, that a defective chip is approaching in 3 feet or 0.006 seconds. The sorting equipment then rejects the defective chip by contacting the defective chip with a blast of air as the chip is launched across an opening of about 12 inches in width between the transport conveyor to a receiving/slow down chute. The air blast deflects the defective chip from the conveyor and into a waste stream.

One advantage for having a short distance between the detection zone and the rejection nozzles is that chips moving at high velocities, meaning speeds of greater than about 500 feet per minute exhibit aerodynamics and can move relative to the targeting information that is transmitted to the air rejection nozzles. Any movement in relative position of the chip can result in either a missed shot or possibly rejecting an adjacent non-defective chip. An advantage of placing the vision units as close as possible to the rejection nozzles is that the theoretical probability of missed chips or false rejections is reduced. In one embodiment, image is captured during the "flight" of the chip between the transport conveyor and the slow down chute. In those cases, the distance is probably on the order of less than a foot between the image acquisition system and the ejection nozzles.

Though the present invention has been described with reference to a potato chip production line and soft center defects in potato chips, it is to be understood that the invention is applicable to other defects a familiar to the potato processing industry, and other thermally processed food products, such as baked or fried corn chips, tortilla chips, crackers, etc. The examples and explanations given are not meant to limit the present invention.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

We claim:

1. A method for detecting defects in a process producing food products having a processing unit, said method comprising the steps of:
    capturing an image of said food products in a visible spectrum;
    performing multivariate image analysis on said image to reveal a data set;
    determining whether a defect exists based on said data set;
    wherein said defect occurs when said food products comprise a moisture content of more than about 2.0% by weight;
    wherein said defect exists when said data set reveals at least about 10% of an imaged area of said imaged food products comprises a soft center; rejecting said food products that comprise said defects; and
    wherein said multivariate image analysis occurs by an algorithm programmed into a field programmable gate array.

2. The method of claim 1 further comprising the step of adjusting a process variable to provide a lowered number of said defects.

3. The method of claim 1 wherein said data set comprises a t1-t2 score space.

4. The method of claim 1 further comprising the step of counting the food products that comprise said defects.

5. The method of claim 1 wherein said defect further comprises an acrylamide defect.

6. The method of claim 5 wherein said acrylamide defect further comprises a sugar defect.

7. A method for detecting defects in a process producing food products having a processing unit, said method comprising the steps of:
    capturing an image of said food products in a visible spectrum;
    performing multivariate image analysis on said image to reveal a data set;
    rejecting food products that contain defects, wherein said defects comprise food products with a pre-determined moisture content;

measuring said food products rejected for non-defective food product;

tuning said dataset based upon non-defective food products measured in said rejected food products; and wherein said multivariate image analysis occurs by an algorithm programmed into a field programmable gate array.

8. The method of claim 7 further comprising the step of determining whether a defect exists based on said data set before said rejecting step.

9. The method of claim 7 further comprising the step of sending a signal to downstream sorting equipment to reject the food products comprising said defect before said rejecting step.

10. The method of claim 7 further comprising the step of measuring said food products not rejected at said rejecting step for defective food products.

11. The method of claim 10 further comprising the step of tuning said dataset based upon defective food products measured in a non-rejected food product stream.

12. An apparatus for monitoring a process producing food products for defects comprising:

a processing unit;

an image capturing device;

a computing device configured to store an algorithm, wherein said algorithm transforms a color image of said food products into a $t_1$-$t_2$ score space via multivariate image analysis;

determines if a defect exists based on a resulting data set, wherein said defect exists when said data set reveals at least about 10% of an imaged area of said imaged food products comprises a soft center;

rejects said food products that comprise said defects; and wherein said multivariate image analysis occurs by said algorithm being programmed into a field programmable gate array.

13. The apparatus of claim 12 wherein said computing device comprises a plurality of computer processing arrays that segments said color image.

* * * * *